(12) United States Patent
Xia

(10) Patent No.: US 8,231,588 B2
(45) Date of Patent: *Jul. 31, 2012

(54) METHODS FOR AMELIORATING PAIN AND DEVICES FOR DELIVERING A MEDICAMENT

(76) Inventor: Tian Xia, Chicago, IL (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/414,300

(22) Filed: Mar. 30, 2009

(65) Prior Publication Data
US 2010/0030188 A1 Feb. 4, 2010

Related U.S. Application Data

(63) Continuation-in-part of application No. 12/184,358, filed on Aug. 1, 2008, now abandoned.

(51) Int. Cl.
*A61M 31/00* (2006.01)
(52) U.S. Cl. ........ 604/275; 604/74; 604/187; 604/94.01
(58) Field of Classification Search .................. 604/275, 604/74, 181, 187, 94.01
See application file for complete search history.

(56) References Cited

U.S. PATENT DOCUMENTS

| | | | | |
|---|---|---|---|---|
| 1,755,754 | A | * 4/1930 | Wappler et al. | ............... 604/37 |
| 4,767,416 | A | * 8/1988 | Wolf et al. | ................. 604/239 |
| 4,886,493 | A | 12/1989 | Yee | |
| 5,637,092 | A | 6/1997 | Shaw | |
| 5,642,730 | A | 7/1997 | Baran | |
| 5,817,073 | A | 10/1998 | Krespi | |
| 5,964,223 | A | 10/1999 | Baran | |
| 6,079,413 | A | 6/2000 | Baran | |
| 6,322,542 | B1 | 11/2001 | Nilson et al. | |
| 6,350,465 | B1 | 2/2002 | Jonnalagadda et al. | |
| 6,413,499 | B1 | 7/2002 | Clay | |
| 6,432,986 | B2 | 8/2002 | Levin | |
| 6,491,940 | B1 | 12/2002 | Levin | |

(Continued)

FOREIGN PATENT DOCUMENTS

CA 2266958 * 10/1999

(Continued)

OTHER PUBLICATIONS

International Search Report from corresponding International Application No. PCT/US2009/051139 dated Dec. 1, 2009. pp. 1-5.

(Continued)

*Primary Examiner* — Bhisma Mehta
*Assistant Examiner* — Edelmira Bosques
(74) *Attorney, Agent, or Firm* — Brinks Hofer Gilson & Lione

(57) ABSTRACT

A method for delivering medicament such as for ameliorating pain in a patient includes introducing an injector through a nasal passage of the patient into a region substantially medial and/or posterior and/or inferior to a sphenopalatine ganglion (SPG) of the patient; and delivering a medicament from the injector superiorly and/or laterally and/or anteriorly towards the SPG. A device for delivering a medicament to a patient in need thereof includes (a) an injector containing a first end configured to remain outside a nasal passage of the patient and a second end configured for entry into the nasal passage of the patient; and (b) an introducer configured for engagement with a nostril of the patient and containing a passageway configured for slidably receiving the injector. The injector is moveable between a storage position preceding the engagement and an engaging position pursuant to the engagement.

30 Claims, 4 Drawing Sheets

U.S. PATENT DOCUMENTS

| | | | |
|---|---|---|---|
| 6,526,976 | B1 | 3/2003 | Baran |
| 6,729,334 | B1 | 5/2004 | Baran |
| 7,469,700 | B2 | 12/2008 | Baran |
| 7,472,705 | B2 | 1/2009 | Baran |
| 2001/0004644 | A1 | 6/2001 | Levin |
| 2001/0055607 | A1 | 12/2001 | Levin |
| 2002/0010194 | A1 | 1/2002 | Levin |
| 2003/0133877 | A1 | 7/2003 | Levin |
| 2005/0072430 | A1 | 4/2005 | Djupesland |
| 2005/0281751 | A1 | 12/2005 | Levin |
| 2010/0030188 | A1 | 2/2010 | Xia |

FOREIGN PATENT DOCUMENTS

| | | | |
|---|---|---|---|
| GB | | 2 435 835 A | 9/2007 |
| WO | WO 2008/122791 A2 | | 10/2008 |

OTHER PUBLICATIONS

International Preliminary Report on Patentability from corresponding International Application No. PCT/US2009/051139, 8pp., dated Feb. 10, 2011. pp. 1-8.

Brown, L.A. "Mythical Sphenopalatine Ganglion Neuralgia," *Southern Medical Journal*, 1962, 55, 670-672.

Diamond, S.; Elkind, A.; Jackson, R.T.; Ryan, R.; DeBussey, S.; Asgharnejad, M. "Multiple-Attack Efficacy and Tolerability of Sumatriptan Nasal Spray in the Treatment of Migraine," *Arch Fam Med*, 1998, 7, 234-240.

Fink, J.B.; Simon, M.; Klimowicz, M. "Budesonide Administration with a Novel Aerosol Generator: An *In Vitro* Evaluation," *American Thoracic Society 97th International Conference*, 2001, San Francisco, CA, 4 pages.

Foo, M.Y.; Cheng, Y-S.; Su, W-C.; Donovan, M.D. "The Influence of Spray Properties on Intranasal Deposition," *Journal of Aerosol Medicine*, 2007, 20(4), 495-508.

Geller, D.E.; Rosenfeld, M.; Waltz, D.A.; Wilmott, R.W. "Efficiency of Pulmonary Administration of Tobramycin Solution for Inhalation in Cystic Fibrosis Using an Improved Drug Delivery System," *Chest Journal*, 2003, 123, 28-36.

Kanai, A.; Suzuki, A.; Kobayashi, M.; Hoka, S. "Intranasal Lidocaine 8% Spray for Second-Division Trigeminal Neuralgia," *British Journal of Anaesthesia*, 2006, 97(4), 559-563.

Klein, R.N.; Burk, D.T.; Chase, P.F. "Anatomically and Physiologically Based Guidelines for Use of the Sphenopalatine Ganglion Block Versus the Stellate Ganglion Block to Reduce Atypical Facial Pain," *Journal of Craniomandibular Practice*, 2001, 19(1), 48-55.

Maizels, M. "Intranasal Lidocaine to Prevent Headache Following Migraine Aura," *Headache*, 1999, 39, 439-442.

Noorily, A.D., Noorily, S. H. and Otto, R. A., "Cocaine, Lidocane, Tetracaine: Which is Best for Topical Nasal Anesthesia?". Anesth Analg, 1995, 724-727.

Peterson, J.N.; Schames, J.; Schames, M.; King, E. "Sphenopalatine Ganglion Block: A Safe and Easy Method for the Management of Orofacial Pain," *Journal of Craniomandibular Practice*, 1995, 13(3), 177-181.

Prasanna, A.; Murthy, P.S.N. "Sphenopalatine Ganglion Block and Pain of Cancer," *Letters*, 1993, 8(3) 125.

Randall, T., Yli-Hankala, A., Valli, H. and Lindgren, L., "Topical Anaesthesia of the Nasal Mucosa for Fibreoptic Airway Endoscopy,", British Journal of Anaesthesia, 1992, 68: 164.197.

Sanders, M.; Zuurmond, W.W.A. "Efficacy of Sphenopalatine Ganglion Blockade in 66 Patients Suffering from Cluster Headache: a 12- to 70-Month Follow-Up Evaluation," *J. Neurosurg.*, 1997, 87, 876-880.

Saper, J.R.; Klapper, J.; Mathew, N.T.; Rapoport, A.; Phillips, S.B.; Bernstein, J.E. "Intranasal Civamide for the Treatment of Episodic Cluster Headaches," *Arch Neurol.*, 2002, 59, 990-994.

Scheibe, M.; Bethge, C.; Witt, M.; Hummel, T. "Intranasal Administration of Drugs," *Arch Otolaryngol Head Neck Surg.*, 2008, 134(6), 643-646.

Torelli, P.; Manzoni, G.C. "Cluster Headache: Symptomatic Treatment," *Neurol. Sci.*, 2004, 25, S119-S122.

Vallejo, R.; Benyamin, R.; Yousuf, N.; Kramer, J. "Computed Tomography-Enhanced Sphenopalatine Ganglion Blockade," *Pain Practice*, 2007, 7(1), 44-46.

Varghese, B.T.; Koshy, R.C. "Endoscopic Transnasal Neurolytic Sphenopalatine Ganglion Block for Head and Neck Cancer Pain," *Journal of Laryngology & Otology*, 2001, 115(5), 385-387.

Varghese, B.T.; Koshy, R.C.; Sebastian, P.; Joseph, E. "Combined Sphenopalatine Ganglion and Mandibular Nerve, Neurolytic Block for Pain Due to Advanced Head and Neck Cancer," *Palliative Medicine*, 2002, 16, 447-448.

Wahl, K.J.; Otsuji, A. "New Medical Management Techniques for Acute Exacerbations of Chronic Rhinosinusitis," *Current Opinion in Otolaryngology & Head and Neck Surgery*, 2003, 11, 27-32.

Weingarten, C. Z., "Injection of the Pterygopalatine Fossa with Glycerin for Posterior Epistaxis," Department of Surgery, Division of Otolaryngology, Michael Reese Hospital and Medical Center, Presented at the Seventy-sixth Annual Meeting of the American Academy of Ophthalmology and Otolaryngology, Las Vegas, NV, 1971, 932-937.

Windsor, R.E.; Janke, S. "Sphenopalatine Ganglion Blockade: A Review and Proposed Modification of the Transnasal Technique," *Pain Physician*, 2004, 7, 283-286.

Yang, I.Y.; Oraee, S. "A Novel Approach to Transnasal Sphenopalatine Ganglion Injection," *Pain Physician*, 2006, 9, 131-134.

"This Month in Archives of Neurology," Arch Neurol. 2006, 63, 1523-1524.

Waldman, S. D., Bloch, J. I. and Duckwall, C. H., "Chapter 3, sphenopalatine Ganglion Block: Transnasal Approach," 2003, 10-12.

ENT Product Marketplace, ENT-Ear, Nose & Throat Journal, Jul. 2002, 470.

Office Action from corresponding U.S. Appl. No. 12/414,300, dated Sep. 11, 2009.

Written Opinion from corresponding Singaporean Patent Application No. 201100695-4, dated 6pp., Jul. 7, 2011.

International Search Report for International Application No. PCT/US2011/058238, dated Jan. 30, 2012, 1 page.

Written Opinion of the International Searching Authority for International Application No. PCT/US2011/058238, dated Jan. 30, 2012, 5 pages.

* cited by examiner

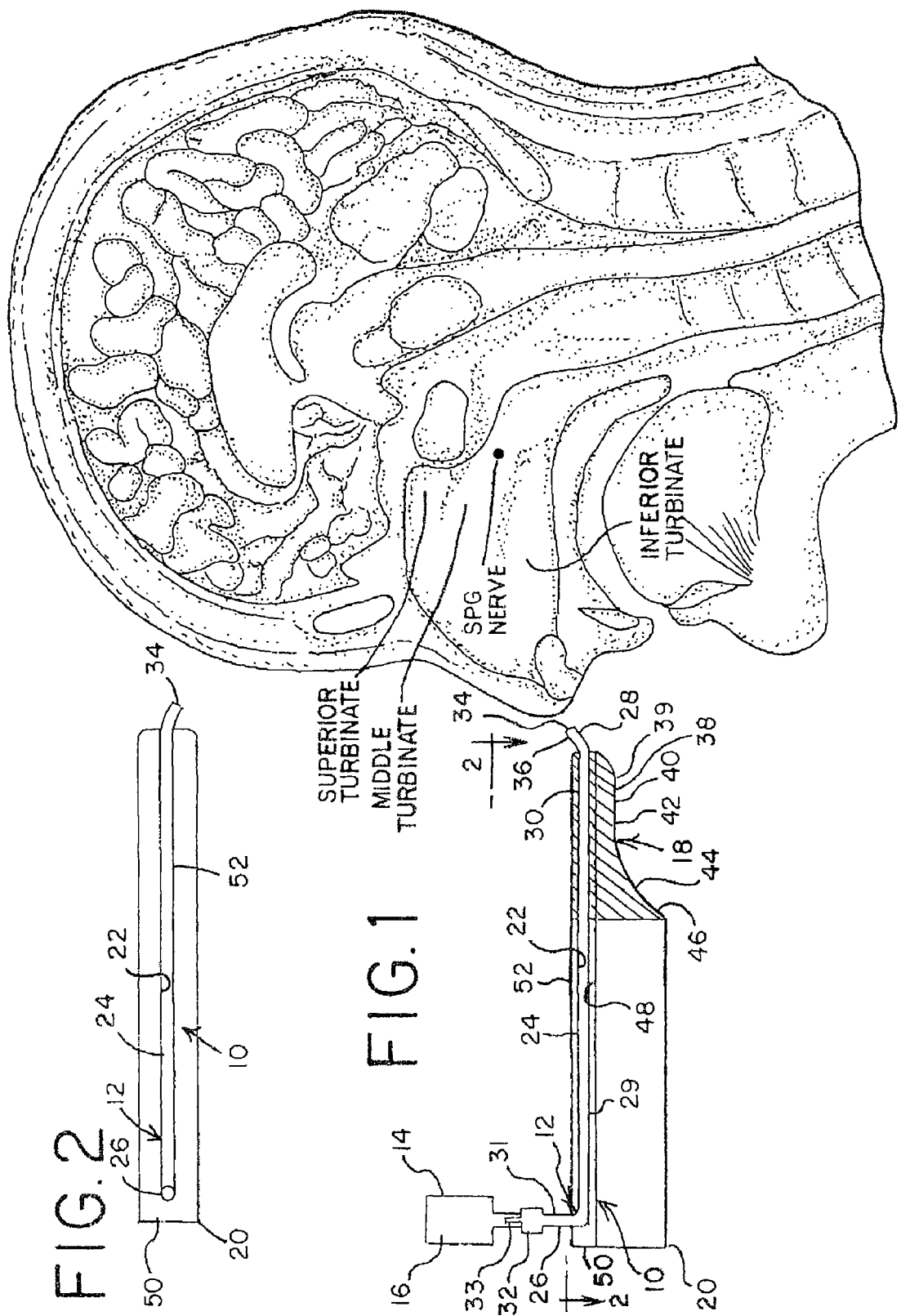

METHODS FOR AMELIORATING PAIN AND DEVICES FOR DELIVERING A MEDICAMENT

RELATED APPLICATIONS

This application is a continuation-in-part of prior application Ser. No. 12/184,358, filed Aug. 1, 2008 now abandoned. The entire contents of the prior application are incorporated herein by reference, except that in the event of any inconsistent disclosure or definition from the present application, the disclosure or definition herein shall be deemed to prevail.

TECHNICAL FIELD

The embodiments described herein relate generally to devices and methods for delivering medicament—particularly, though not exclusively, to delivering medicament for the management of pain associated with headaches, facial aches, and the like.

INTRODUCTION

Conventional methods for treating pain associated with headaches and facial aches are not as safe or effective as desired. By way of example, non-steroidal anti-inflammatory drugs (NSAIDs), such as the COX-2 brand of medications, must be used sparingly and only for short durations in view of their potential for causing ulcers and heart attacks—a drawback that is further compounded by the inefficacy of these medications in a large number of patients. The use of narcotics is likewise undesirable in view of their potentially addictive properties. In addition, the use of tryptamine-based drugs—which include but are not limited to sumatriptan (sold under the tradename IMITREX by GlaxoSmithKline) and zolmitriptan (sold under the tradename ZOMIG by AstroZeneca)—is undesirable in view of the costliness and potentially high toxicity of these drugs.

One method that has been employed for controlling the pain associated with headaches and facial aches is known as an SPG block. In this approach, anesthetic is applied to a sphenopalatine ganglion (SPG) of a patient by a trained medical professional, who typically inserts a cotton-tipped applicator soaked in the anesthetic into the nostril of a patient in order to apply the anesthetic to the SPG. Using the middle turbinate as an anatomical landmark, the soaked cotton-tipped applicators are pushed upwards in what is essentially a blind advance (the success of which depends very heavily on the skill and experience of the physician). Clearly, the efficacy and safety of this procedure leave much to be desired. Moreover, the efficacy and safety of conventional SPG blocks have been significantly compromised by a long-held but mistaken belief amongst clinicians that the SPG is located posterior to the superior turbinate—which it is not.

SUMMARY

The scope of the present invention is defined solely by the appended claims, and is not affected to any degree by the statements within this summary.

A first method for ameliorating pain in a patient includes introducing an injector through a nasal passage of the patient into a region substantially medial and/or posterior and/or inferior to a sphenopalatine ganglion of the patient; and delivering a medicament from the injector superiorly and/or laterally and/or anteriorly towards the sphenopalatine ganglion.

A first device for delivering a medicament to a patient in need thereof includes (a) an injector containing a first end configured to remain outside a nasal passage of the patient and a second end configured for entry into the nasal passage of the patient; and (b) an introducer configured for engagement with a nostril of the patient and containing a passageway configured for slidably receiving the injector.

A second device for delivering a medicament to a patient in need thereof includes (a) an injector containing a first end configured to remain outside a nasal passage of the patient, a second end configured for entry into the nasal passage of the patient, and a channel extending from the first end to the second end and configured for receiving a medicament, wherein the second end of the injector contains one or a plurality of apertures configured for dispersing a medicament superiorly, laterally, and anteriorly towards a sphenopalatine ganglion; (b) an introducer configured for engagement with a nostril of the patient and containing a passageway configured for slidably receiving the injector, a first portion contoured such that it is configured to be complementary in shape to an interior of the nostril, and a second portion containing a rounded convex portion and a substantially flat underside, wherein a cross-sectional area of the first portion is larger than a cross-sectional area of the second portion; and (c) a handle connected to the introducer and containing a track configured to receive the passageway of the introducer. The handle is configured for movement towards the patient's face, such that posterior movement of the handle moves the introducer into engagement with the nostril of the patient. The injector is moveable between a storage position preceding the engagement and an engaging position pursuant to the engagement, wherein the engaging position is situated medial, posterior, and inferior to the sphenopalatine ganglion.

A second method for ameliorating pain in a patient includes delivering a medicament superiorly and/or laterally and/or anteriorly towards the sphenopalatine ganglion using a device as described herein.

BRIEF DESCRIPTION OF THE DRAWINGS

FIG. 1 shows a cross-sectional side view of a device for delivering a medicament to a patient in need thereof prior to insertion of the device into a patient's nostril in accordance with principles described herein.

FIG. 2 shows a cross-sectional top plan view of the device of FIG. 1 taken along the line 2-2.

DETAILED DESCRIPTION

Heretofore unknown and highly effective methods for ameliorating pain in a patient—particularly though not exclusively the pain associated with headaches, facial aches, and the like—and user-friendly devices enabling facile administration of medicaments in accordance with these methods, have been discovered and are described herein. As further explained below, the methods and devices described herein enable delivery of a medicament superiorly and/or laterally and/or anteriorly towards the sphenopalatine ganglion from a region substantially medial and/or posterior and/or inferior to the sphenopalatine ganglion. The methods and devices may provide patients and clinicians a safe and effective way to achieve an SPG block—particularly ones that can be employed by a clinician and/or directly by a patient without the assistance or supervision of a trained medical professional.

As used herein, the phrase "towards the sphenopalatine ganglion" and similar such phrases used in reference to the delivery of a medicament are intended to include the SPG itself as well as the pterygopalatine fossa which houses the SPG and the sphenopalatine foramen.

Figure 5:
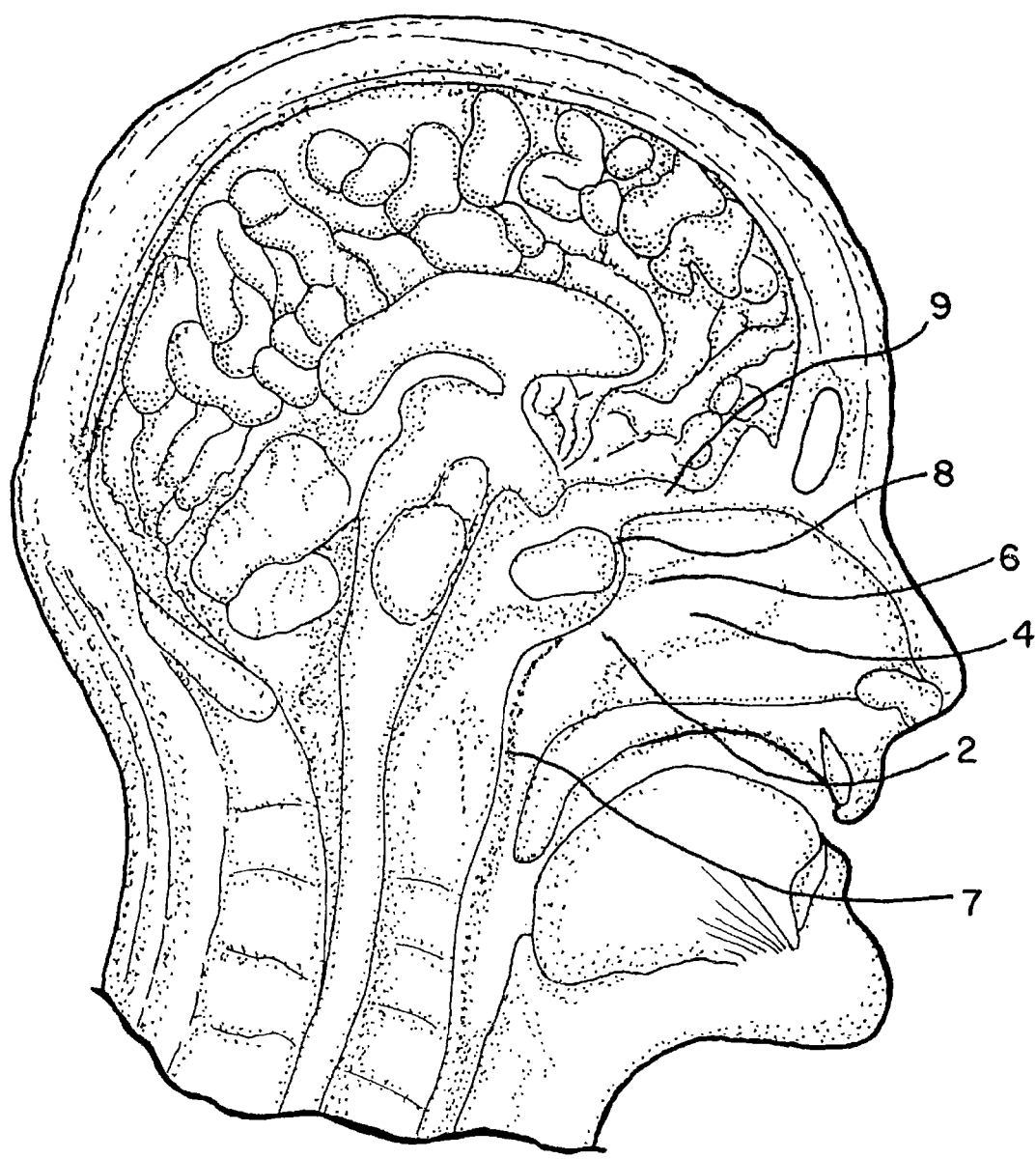
FIG. 5 shows a median cross-sectional view of a human head with the SPG 2 shown in its correct anatomical position posterior to the middle turbinate 4.

By way of introduction, FIG. 5 shows a median cross-sectional view of a human head that correctly identifies the location of the SPG 2 as being posterior to the middle turbinate 4—not posterior to the superior turbinate 6 or at the apex 8 of the nasal cavity in proximity to cribriform plate 9 as various clinicians have erroneously thought. In addition, the correct location of the SPG 2 is actually offset laterally from the plane of the drawing—in other words, the SPG does not lie in a two-dimensional plane with respect to the depicted cross-section, as has also been erroneously held by various clinicians.

Figure 3:
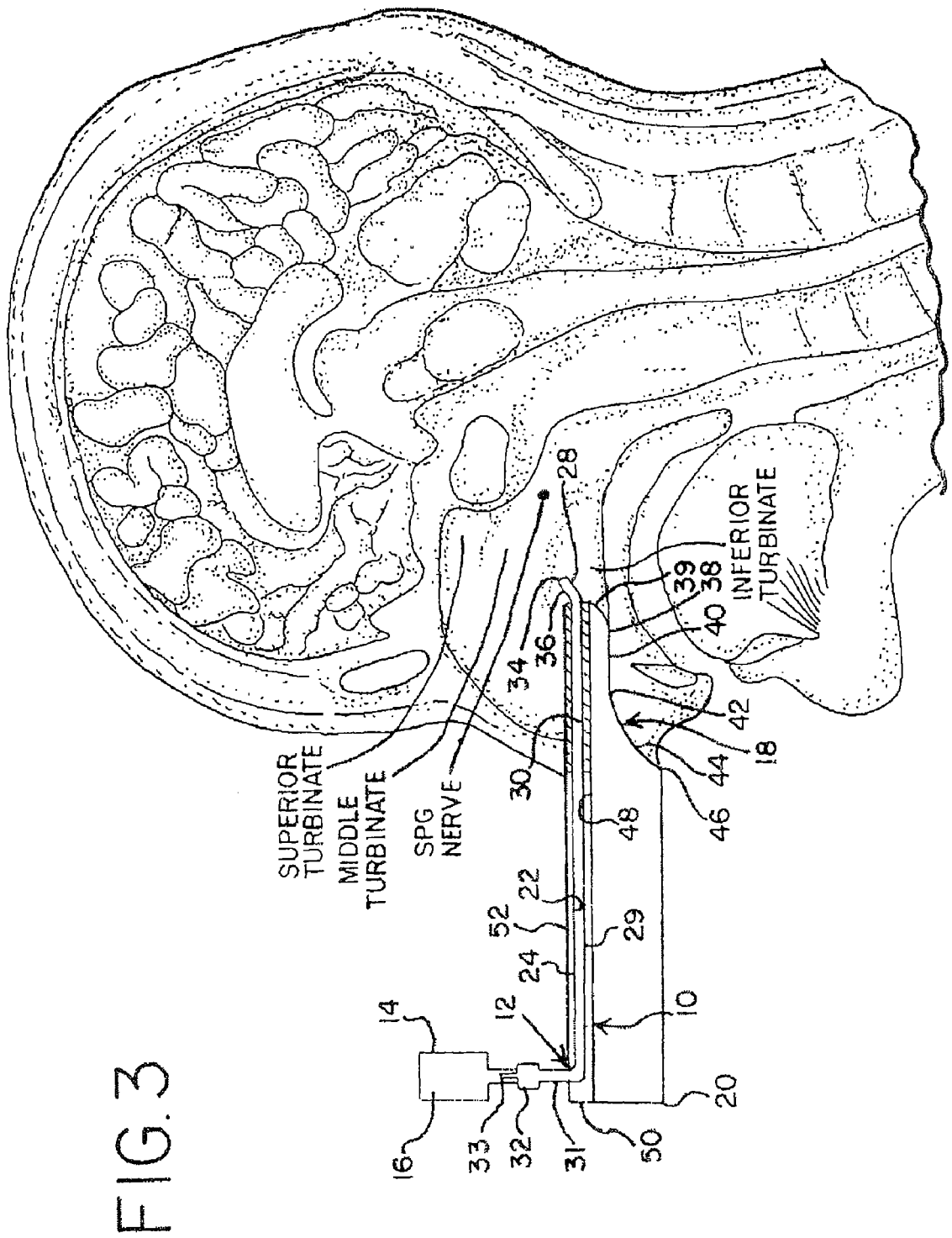
FIG. 3 shows a cross-sectional side view of the device of FIG. 1 after the introducer has been engaged with a patient's nostril in accordance with principles described herein.

In U.S. Pat. No. 4,886,493, Jordan Yee describes a process for performing an SPG block in which a tube is inserted through the nostril of a patient in an attempt to deliver medication to the pterygopalatine fossa, which houses the SPG. Unfortunately, as shown in FIG. 3 of U.S. Pat. No. 4,886,493, the location of the pterygopalatine fossa (18) has been misidentified as lying posterior to the superior turbinate and in an x-y plane accessible by a straight line from the nostril via a tube (11). As a result of this misunderstanding—in addition to the expected lack of efficacy one would expect from delivering medication to the wrong location—the terminal end (13) of the Yee device comes perilously close to contacting the delicate cribriform plate. Since the cribriform plate is sieve-like and in communication with the frontal lobe of the brain, it is extremely dangerous to introduce anesthetics in close proximity to this plate since they can easily penetrate through to the frontal lobe.

U.S. Pat. No. 6,491,940 B1 to Bruce H. Levin describes an alternative procedure for performing an SPG block. In contrast to the Yee patent described above, U.S. Pat. No. 6,491,940 B1 appears to recognize the lateral offset of the SPG since it describes a curved rather than straight body (100) for introducing anesthetic. Unfortunately, similarly to the Yee patent, the Levin patent also fails to recognize that the correct location of the SPG is posterior to the middle turbinate—not at the apex of the nasal cavity as shown in FIG. 4A of Levin and as described therein (e.g., col. 72, lines 20-22). Thus, as in the case of the Yee patent, the process described in the Levin patent once again introduces an anesthetic delivering device in dangerously close proximity to the cribriform plate with all of the attendant risks and diminished efficacies associated therewith.

U.S. Pat. No. 6,322,542 B1, assigned to AstraZeneca, describes a device for delivering medicaments into the nasal cavity of a patient. Although the stated objective of this device is to effectively deliver medicament to the posterior region of the nasal cavity (col. 1, lines 29-32), its configuration (e.g., the linearity of tubular member 35) is ill-adapted to delivering medicament to or in proximity to the SPG. Rather, medicament will be delivered largely to the region 7 shown in FIG. 5 of the present application. The delivery of anesthetics in proximity to the region 7 is highly undesirable inasmuch as the anesthetics can readily suppress the gag reflex, thereby creating a risk of aspiration pneumonia.

While neither desiring to be bound by any particular theory, nor intending to affect in any measure the scope of the appended claims or their equivalents, the following background information is provided regarding present-day understanding of the anatomy of the SPG in order to further elucidate the description of the devices and methods provided hereinbelow.

The SPG (also known as the pterygopalatine ganglion) is the largest group of neurons outside the cranial cavity and lies in the pterygopalatine fossa, which is approximately 1-cm wide and approximately 2-cm high. The pterygopalatine fossa is bordered anteriorly by the posterior wall of the maxillary sinus, posteriorly by the medial plate of the pterygoid process, medially by the perpendicular plate of the palatine bone, and superiorly by the sphenoid sinus. Laterally, the pterygopalatine fossa communicates with the infratemporal fossa.

The SPG within the fossa is located posterior to the middle turbinate of the nose and lies a few millimeters (1 mm to 5 mm) deep to the lateral nasal mucosa. The SPG has a complex neural center and multiple connections. The SPG is suspended from the maxillary branch of trigeminal nerve at the pterygopalatine fossa via the pterygopalatine nerves, and lies medial to the maxillary branch when viewed in the saggital plane. Posteriorly, the SPG is connected to the vidian nerve. The SPG itself has efferent branches and forms the superior posterior lateral nasal and pharyngeal nerves. Caudally, the ganglion (SPG) is in direct connection with the greater and lesser palatine nerves.

The SPG has sensory, motor and autonomic components. The sensory fibers arise from the maxillary nerve, pass through the SPG, and are distributed to the nasal membranes, the soft palate and some parts of the pharynx. A few motor nerves are also believed to be carried with the sensory trunks.

The autonomic innervations of the SPG are more complex. The sympathetic component begins with preganglionic sympathetic fibers originating in the upper thoracic spinal cord, forming the white ramie communicantes, coursing through the sympathetic ganglion, where the preganglionic fibers synapse with the postganglionic ones. The postganglionic fibers then join the carotid nerves before branching off and traveling through the deep petrosal and vidian nerves. The postganglionic sympathetic nerves continue their path through the SPG on their way to the lacrimal gland and nasal and palatine mucosa.

The SPG is usually considered parasympathetic in function. The parasympathetic component of SPG has its preganglionic origin in the superior salivatory nucleus then travels through a portion of the facial nerve (VII) before forming the greater petrosal nerve to form the vidian nerve, which ends in the SPG. Within the ganglion, the preganglionic fibers synapse with their postganglionic cells and continue on to the nasal mucosa, and one branch travels with the maxillary nerve to the lacrimal gland.

Notwithstanding the description above, and regardless of the currently-held theories respecting the anatomy of the SPG, a safe and effective amelioration of pain can be achieved as a result of using the devices and methods described below. Although a representative device 10 will be described in reference to FIGS. 1-4, it is to be understood that this representative device is merely illustrative and that alternative structures can likewise be utilized for delivering a medicament in accordance with principles described herein. It is to be understood that elements and features of the various representative devices described below may be combined in different ways to produce new embodiments that likewise fall within the scope of the present teachings. The drawings and the description below have been provided solely by way of illustration, and are not intended to limit the scope of the appended claims or their equivalents.

Figure 4:
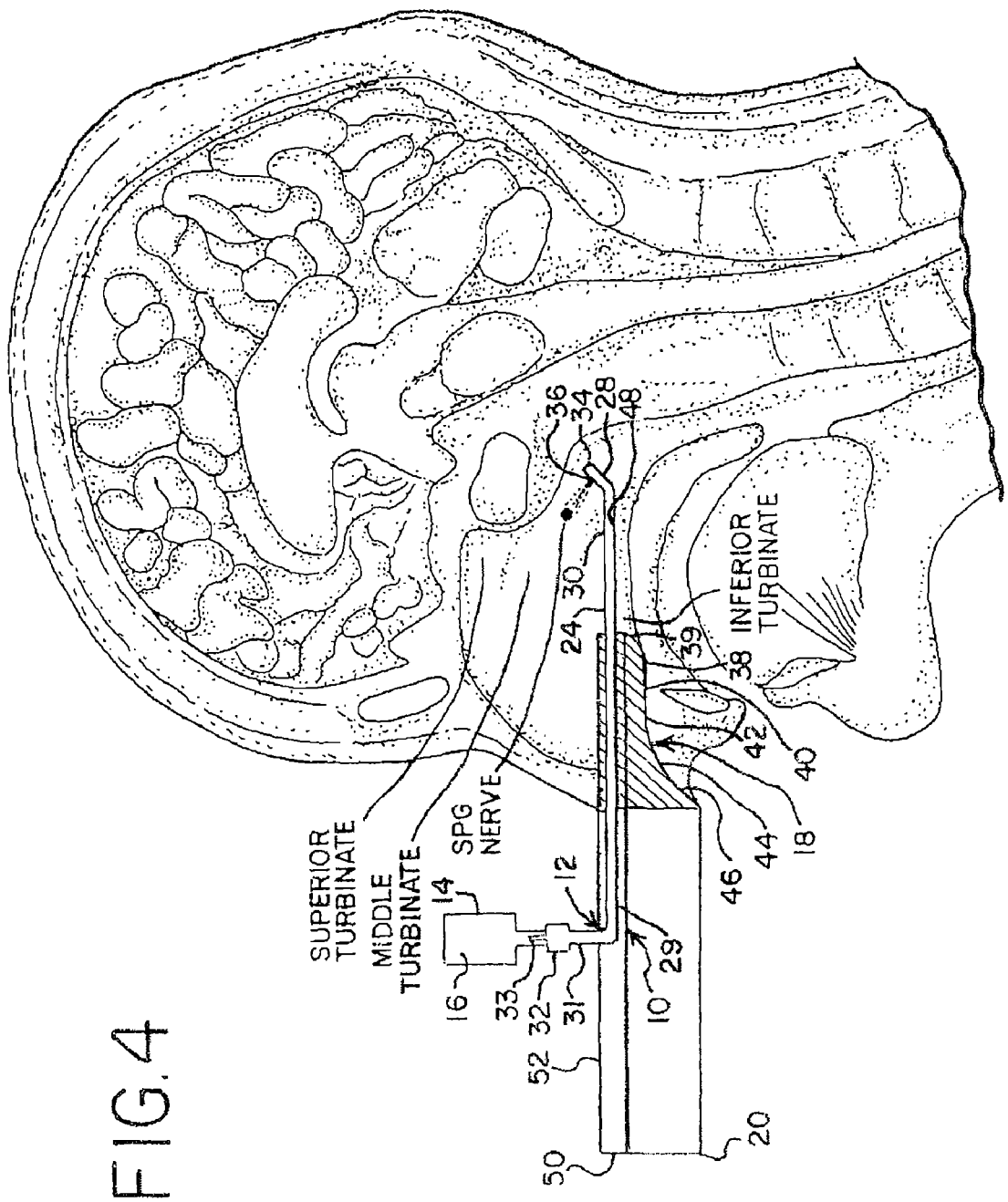
FIG. 4 shows a cross-sectional side view of the device of FIG. 1 after the introducer has been engaged with a patient's nostril and after the injector has been moved from its storage position to an engaging position that positions the second end of the injector medial, posterior, and inferior to the sphenopalatine ganglion.

FIGS. 1-4 show a representative device 10 for delivering a medicament to a patient in need thereof. The device 10 includes an injector 12 comprising a first end 29 configured to remain outside a nasal passage of the patient and a second end 30 configured for entry into the nasal passage of the patient. Device 10 further includes an introducer 18 configured for engagement with a nostril of the patient and comprising a passageway 48 configured for slidably receiving the injector 12. The injector 12 is moveable between a storage position (best shown by FIG. 1) preceding engagement of introducer 18 with a patient's nostril, and an engaging position (best shown by FIG. 4) pursuant to engagement of introducer 18 with the patient's nostril. However, upon the initial engagement of introducer 18 with a patient's nostril, the injector 12 is desirably maintained—at least for a time—in a storage position (best shown by FIG. 3) until it is deliberately moved to an engaging position (best shown by FIG. 4) under the direction of a user. In some embodiments, the engaging position of injector 12 is situated medial and/or inferior to the SPG. In other embodiments, the engaging position of injector 12 is situated medial, inferior, and posterior to the SPG, as best shown by FIG. 4.

As used herein, the phrases "storage position" and "engaging position" are each intended to encompass multiple positions within a selected range. For example, in some embodiments, the degree to which injector 12 is extended into the nostril of a first patient (e.g., a child) will vary from the degree to which injector 12 is extended into the nostril of a second patient (e.g., an adult male). Notwithstanding, the phrase "engaging position" is intended to encompass many variations in the precise position of injector 12 within the nostril, any of which are properly regarded as being medial and/or posterior and/or inferior to the SPG. In some embodiments, injector 12 is not slidable within introducer 18 but rather is fixed in a predetermined position so as to be medial and/or inferior to the SPG upon engagement of introducer 18 with a patient's nostril. In other embodiments, injector 12 is not slidable within introducer 18 but rather is fixed in a predetermined position so as to be medial, posterior, and inferior to the SPG upon engagement of introducer 18 with a patient's nostril.

The injector 12 comprises a tubular section 24 (a so-called cobra tube in recognition of the tube's extensibility) that includes a channel 22 extending from first end 29 to second end 30 and configured for receiving a medicament. In some embodiments, tubular section 24 has an outer diameter of about 5 mm and channel 22 has an inner diameter of about 2 mm. Throughout this description, measurements and distances such as the diameters just given are to be strictly regarded as being merely representative and in no way limiting and/or fixed. Considerable variation in all measurements and distances provided in this description is possible, as will be readily appreciated by one of ordinary skill in the art.

In some embodiments, the second end 30 of injector 12 contains a nozzle 28 having a tip 34 that contains one or a plurality of apertures 36 configured for spraying a medicament superiorly and/or laterally and/or anteriorly towards the SPG. In some embodiments, nozzle 28 is configured for spraying a medicament laterally and/or superiorly towards the SPG, and in other embodiments, nozzle 28 is configured for spraying a medicament laterally, superiorly, and anteriorly towards the SPG.

In some embodiments, nozzle 28 extends at an upward angle of inclination from second end 30 of injector 12. In some embodiments, nozzle 28 extends in a lateral, anterior, and superior direction at an angle of inclination ranging from about 45 degrees to about 60 degrees to accommodate varying patient anatomies in which the SPG resides in a lateral cave posterior to the middle turbinate. In some embodiments, nozzle 28 has a length ranging from about 2 mm to about 5 mm. In some embodiments, injector 12 is designed to exhibit handedness, such that in some embodiments, injector 12 is configured for engagement with a left-side nostril of a patient, whereas in other embodiments, injector 12 is configured for engagement with a right-side nostril of the patient (with the contour of a left-handed injector being generally complementary to the contour of a right-handed injector).

The introducer 18 can be aimed into a nostril to provide a horizontal pathway substantially parallel to the bottom of the nasal cavity or floor of the nose—such that introducer 18 is supported on the bottom of the nasal cavity—to a position medial to the inferior turbinate. This self-seating feature of introducer 18 facilitates quick and accurate usage by a patient without necessitating supervision from a medical professional. In some embodiments, introducer 18 provides an extended pathway of between about 1.5 cm and about 2 cm into the nostril. Once introducer 18 is placed firmly against the nose, the tip of the nose will tend to point superiorly. The tubular section 24 of injector 12 can then be pushed partially or completely into the back of the nostril. In order to accommodate the slightly curved nature of the interior anatomy of the nose, the passageway 48 in which tubular section 24 lies can be curved slightly to the ipsilateral nostril by about 5 to about 20 degrees. Once tubular section 24 is in position, a medicament can then be delivered to the SPG from nozzle 28 to exert the desired SPG blocking effect. In some embodiments, device 10 is provided with an optional safety abutment stop to limit the extent of travel into the nostril available to injector 12.

As best shown by FIGS. 1, 3, and 4, introducer 18 contains a first portion 44 and a second portion 38. In some embodiments, a cross-sectional area of first portion 44 is larger than a cross-sectional area of second portion 38. In some embodiments, first portion 44 is generally concave and has a contour 46 configured to be complementary in shape to an interior of the nostril so as to substantially conform therewith. In some embodiments, narrow second portion 38 has a rounded convex portion 39 and an underside 40 having a generally flat surface 42. The passageway 48 of introducer 18 slidably receives tubular section 24 of injector 12 and, in some embodiments, has a diameter of between about 6 mm and about 7 mm. In some embodiments, second portion 38 of introducer 18 contains a nostril-engaging tip that extends from about 1 cm to about 3 cm. In some embodiments, first portion 44 of introducer 18 extends from about 2 cm to about 3 cm. In some embodiments, introducer 18 is designed to exhibit handedness, such that in some embodiments, introducer 18 is configured for engagement with a left-side nostril of a patient, whereas in other embodiments, introducer 18 is configured for engagement with a right-side nostril of the patient (with the contour of a left-handed introducer being generally complementary to the contour of a right-handed introducer).

In some embodiments, device 10 further includes a container 14 in communication with first end 29 and channel 22 of injector 12, which is configured for holding a medicament 16 (e.g., anesthetic). In some embodiments, as shown in FIGS. 1, 3, and 4, container 14 is supported on a stem 26 having a lower section 31 which, in some embodiments, has an outer diameter substantially the same as that of tubular section 24. Lower section 31 can extend outwardly and/or upwardly and/or at an angle of inclination from first end 29 of injector 12 and, in some embodiments, connects with an upper section 32 having an enlarged diameter configured to receive an outlet 33 of container 14. Analogous to lower section 31, upper section 32 can extend outwardly and/or upwardly and/or at an angle of inclination.

In some embodiments, container 14 is operatively connected, mounted or otherwise secured to upper stem section 32 and is fully or partially filled with a medicament 16. Since container 14 is in communication with channel 22 of injector 12, medicament 16 can be delivered along tubular section 24 and released through one or more apertures 36 of nozzle 28. Container 14 can be formed of plastic, metal or the like, and can be squeezable and/or pressurized to facilitate medicament delivery into channel 22. In some embodiments, container 14 is replaced by a port (not shown), such that a medicament can be introduced through the port into upper section 32 by a delivery device such as a syringe.

In some embodiments, device 10 further includes an optional handle 20 connected to a rear portion of introducer 18 adjacent first portion 44. The handle 20 includes an upwardly facing groove 50 that provides a track 52 configured to receive and in communication with passageway 48 of introducer 18 to slidably receive tubular section 24 of injector 12. In some embodiments, track 52 has a depth or width of between about 6 mm and about 7 mm. Handle 20 is configured for movement towards a patient's face, such that posterior movement of handle 20 moves introducer 18 into engagement with the nostril of the patient.

Injector 12, introducer 18, and handle 20 can be formed from all manner of materials including but not limited to flexible, rigid or semi-rigid polymeric materials (e.g., plastics, rubbers, etc.), metals and alloys thereof, and the like, and combinations thereof. In some embodiments, injector 12 is formed of a flexible plastic, introducer 18 is formed of an elastomeric and/or resilient plastic or rubber, and handle 20 is formed of plastic. In some embodiments, one or more of injector 12, introducer 18, and handle 20 is designed from a material so as to be disposable and/or biodegradable.

While the representative device 10 described above can be used to deliver a medicament superiorly and/or laterally and/or anteriorly towards a sphenopalatine ganglion of a patient in accordance with the principles set forth herein, alternative structures can likewise be employed to similarly accomplish such a delivery.

Solely by way of example, a delivery tube having a curved portion at one of its ends configured for insertion into a patient's nostril—analogous to the angled nozzle 28 provided on the second end 30 of injector 12—can be housed within a substantially cylindrical (e.g., pen- or cigar-shaped) housing. The delivery tube can be formed of a flexible or semi-rigid material (such as a plastic) such that it can be maintained in a substantially linear or non-curved arrangement while in its storage position within the housing but readily restored to its curved configuration when extended from the housing into an engaging position. In such a device, one or more internal surfaces of the external housing acts to straighten or restrain—completely or at least partially—the inherent curvature of the delivery tube until such time as the delivery tube is moved to an engaging position, whereupon the curvature of the tube is restored. In some embodiments, at least a portion of the delivery tube (e.g., the end designed to emit medicament) can be expandable if desired (e.g., when air, oxygen and/or other gases, and/or medicaments are forced through the tube under pressure).

By providing one or more optional indicial markings on the cylindrical housing described above, a user can readily identify the direction of curvature of the delivery tube stored inside, such that by turning the housing around and arc of 360 degrees, the user can select any desired direction of spray for delivering a medicament through the delivery tube. Simply by rotating the housing, the direction of spray can be incrementally changed through a continuous arc between 0 degrees and 360 degrees inclusive. In design, one end of the housing can be fitted with a luer lock configured to engage with a syringe containing the medicament. Alternatively, the end of the housing configured to remain outside the nostril can be fitted with a septum or similar such membrane through which a medicament can be introduced into the delivery tube housed therein.

Numerous other modifications to the delivery devices described herein, as well as alternative structures, are likewise contemplated for use to the extent they similarly allow for the delivery of a medicament superiorly and/or laterally and/or anteriorly towards a sphenopalatine ganglion of a patient in accordance with the present teachings. By way of example, the portion of the device configured for insertion into a patient's nostril (e.g., a portion of the injector 12 described above) can be formed from any therapeutically acceptable malleable material (e.g., plastics, metals, metal alloys, and the like) capable of receiving and retaining a desired shape when manipulated by a user. (e.g., increased or decreased curvature of the angled nozzle 28 provided on the second end 30 of injector 12). Such a feature may be desirable, for example, when a clinician wishes to customize the exact geometry of a device before using it on a patient in a clinical setting.

A method for ameliorating pain in a patient in accordance with the present teachings includes delivering a medicament superiorly and/or laterally and/or anteriorly towards a sphenopalatine ganglion of a patient using a device as described herein. In some embodiments, the medicament is delivered laterally and/or superiorly towards the SPG. In other embodiments, the medicament is delivered laterally, superiorly, and anteriorly towards the SPG.

In some embodiments, a method for ameliorating pain in a patient includes (a) introducing an injector 12 through a nasal passage of the patient into a region substantially medial and/or posterior and/or inferior to an SPG of the patient; and (b) delivering a medicament from injector 12 superiorly and/or laterally and/or anteriorly towards the SPG. In some embodiments, injector 12 is introduced through a nasal passage of the patient into a region substantially medial and/or inferior to the SPG, whereas in other embodiments the injector 12 is introduced into a region substantially medial, inferior, and posterior to the SPG. In some embodiments, the medicament is delivered laterally and/or superiorly towards the SPG, whereas in other embodiments, the medicament is delivered laterally, superiorly, and anteriorly towards the SPG. In some embodiments, injector 12 has a second end 30 containing one or a plurality of apertures 36 through which a medicament is sprayed towards the SPG.

In some embodiments, injector 12 is slidably received in an introducer 18, as described above, and the method further includes (c) engaging introducer 18 with a nostril of the patient, such that a portion of the patient's nose is lifted upon engagement with introducer 18; and (d) sliding injector 12 from a storage position to an engaging position after introducer 18 is engaged with the nostril. As described above, the engaging position of injector 12 is situated medial and/or posterior and/or inferior to the SPG—medial and/or inferior in some embodiments, and medial, inferior, and posterior in other embodiments. In some embodiments, the medicament is provided in a container 14 connected to and in communication with injector 12, as described above, and the method further includes (e) squeezing container 14 containing the medicament in order to spray the medicament towards the SPG.

In some embodiments, the method includes pushing introducer 18 snugly and comfortably within a nostril to lift the tip of the patient's nose before positioning the nozzle 28 of injector 12 in proximity to the SPG, sliding tubular section 24 of injector 12 through passageway 48 in introducer 18, and/or sliding tubular section 24 of injector 12 on a track 52 of handle 20.

All manner of medicaments suitable for introduction at or in the vicinity of the SPG are contemplated for use in accordance with the present teachings. The physical state of the medicament includes but is not limited to liquids, solids, semi-solids, suspensions, powders, pastes, gels, and the like, and combinations thereof. In some embodiments, the medicament is provided in an at least partially liquid form. In some embodiments, the medicament contains an anesthetic.

Anesthetics that may be used in accordance with embodiments described herein include but are not limited to ambucaine, amolanone, amylocaine, benoxinate, betoxycaine, biphenamine, bupivacaine, butacaine, butamben, butanilicicaine, butethamine, butoxycaine, carticaine, cocaethylene, cocaine, cyclomethycaine, dibucaine, dimethisoquin, dimethocaine, diperodon, dyclonine, ecgonidine, ecgonine, ethyl aminobenzoate, ethyl chloride, etidocaine, β-eucaine, euprocin, fenalcomine, fomocaine, hexylcaine, hydroxyprocaine, hydroxytetracaine, isobutyl p-aminobenzoate, leucinocaine mesylate, levoxadrol, lidocaine, meperidine, mepivacaine, meprylcaine, metabutoxycaine, methyl chloride, myrtecaine, naepaine, octacaine, orthocaine, oxethazaine, parethoxycaine, phenacaine, phenol, a pipecoloxylidide, piperocaine, piridocaine, polidocanol, pramoxine, sameridine, prilocaine, propanocaine, proparacaine, propipocaine, propoxycaine, pseudococaine, pyrrocaine, quinine urea, risocaine, ropivacaine, salicyl alcohol, tetracaine, tolycaine, trimecaine, veratridine, zolamine, and the like, and combinations thereof, as well as all optical and/or stereoisomers thereof, and all pharmaceutically acceptable salts thereof.

In some embodiments, the medicament comprises an anesthetic selected from the group consisting of benzocaine, tetracaine, ropivacaine, lidocaine, water, saline, and combinations thereof. In some embodiments, the medicament comprises water and/or saline having a temperature of less than about 10° C. and in other embodiments of less than about 5° C. In some embodiments, the medicament comprises water and/or saline having a temperature of about 4° C. In some embodiments, the medicament comprises a combination of benzocaine, tetracaine, and ropivacaine. In some embodiments, the medicament comprises an anesthetic comprising about 14% benzocaine, about 2% tetracaine, and about 1% ropivacaine by weight based on total weight of the anesthetic.

In some embodiments, a mixture of benzocaine, tetracaine, and ropivacaine is used to achieve a fast onset of SPG block as well as to prolong the effects of pain relief, thereby reducing the need for repeated applications and minimizing any potential dose-related complications and/or side effects. Benzocaine—which is quite effective in topical use and has a toxic dose in excess of about 200 mg—has an onset time of about 30 seconds and lasts for between about 0.5 and about 1 hour. Benzocaine provides an almost immediate onset of pain relief and may increase the absorption of other local anesthetics when mixed therewith. Ropivacaine—which has a toxic dose of about 175 mg—typically has a slow onset but lasts for between about 2 and about 6 hours. Ropivacaine provides an extended nerve block and lasting pain relief. Tetracaine is a very intense local anesthetic having a fast onset and lasting for between about 0.5 and about 1 hour. When tetracaine is combined with ropivacaine, the duration of pain relief exceeds 6 hours.

In some embodiments, the medicament used in accordance with the present teachings is provided in a container 14 (shown in FIGS. 1, 3, and 4) as a pressured or aerosolized mixture. The medicament optionally contains preservatives, a liquid carrier, and/or other inert ingredients and additives as will be readily appreciated by those of ordinary skill in the art.

The amount of medicament delivered in accordance with the present teachings can be readily determined by one of ordinary skill in the art and will vary according to factors such as the nature and/or concentration of the medicament, the patient's age, condition, and/or sensitivity to the medicament, and the like. In some embodiments, the dosage of anesthetic ranges from about 0.1 cc to about 1.0 cc. In some embodiments, the dosage of anesthetic is about 0.5 cc.

Methods and devices described herein are contemplated for use in the treatment of all manner of conditions for which the introduction of a medicament superiorly and/or laterally and/or anteriorly towards the SPG of a patient is desirable. Representative conditions that can be treated include but are not limited to sphenopalatine neuralgia, trigeminal neuralgia including glossopharyngeal neuralgia, migraine with or without aura, tension headaches, cluster headaches including chronic cluster headaches, paroxysmal hemicranias, superior laryngeal neuralgia, atypical facial pain, herpes zoster opthalmicus, vasomotor rhinitis, major depression, fibromyalgia, and the like, and combinations thereof.

Topical administrations of a medicament to human tissue for the systemic delivery of a pharmaceutically active agent typically include the use of transdermal and/or transmucosal pastes, creams, liquids, solids, semisolids, and the like. However, systemic delivery of pharmaceutically active agents by topical administration is hampered by the difficulty of diffusing an agent through the tissue to which the agent is applied in order to reach blood vessels, whereby the agent can then be absorbed for systemic delivery. Thus, to address this difficulty, the methods and devices described herein may be invoked to achieve increased permeability of the blood brain barrier in the administration of any medicament.

Conventional SPG block procedures have been used to treat a wide array of patient ailments, and the methods and devices described herein are contemplated for use in the treatment of all of them. Representative ailments include but are not limited to the pain and/or discomfort associated with muscle spasm, vascospasm, neuralgia, reflex sympathetic dystrophy, chronic low back pain of multiple etiology (e.g., muscular, discogenic, arthritic, etc.), external cricoidynia, lower jaw toothache, glossodynia, earache (in case of Eustachian tube) and middle ear lesions, earache secondary to cancer of the larynx, pain from laryngeal tuberculosis, spasm of the face and upper respiratory tract, syphilitic headache, malarial headache, cluster headache, ophthalmic migraine, dysmenorrheal, intercostal pain (neuralgia), gastric pain, nausea and diarrhea, myalgias of the neck muscles, sciatica, maxillary neuralgia, sensory facial neuralgia, upper teeth pain, pain associated with tooth extraction, feeling of foreign body in the throat, persistent itching in the external ear canal, herpes zoster oticus, taste disturbances, atypical facial pain, tic douloureux, cervical arthritis, myofascial syndrome, peripheral neuropathy, post-herpetic neuralgia, fracture secondary to osteoporosis, lumbosacral strain, extremity arthritis, various other arthritic conditions, and the like, and combinations thereof. Further indications for which the devices and methods described herein are contemplated include but are not limited to rage control, depression amelioration, and the like.

The term "kit" refers to an assembly of materials that are used in performing a method in accordance with the present teachings. Such kits can include one or a plurality of devices and/or components thereof, including but not limited to the representative devices described above, and may further include one or more medicaments to be used therewith, including but not limited to one or a plurality of the anesthetics described above.

In some embodiments, a kit includes an injector and/or an introducer, each of which is configured for engagement with a left-side nostril of the patient. In some embodiments, a kit includes an injector and/or an introducer configured for engagement with a right-side nostril of the patient. In some embodiments, a kit includes an injector and an introducer configured for engagement with a left-side nostril of the patient, as well as an injector and an introducer configured for engagement with a right-side nostril of the patient. Optionally, an interchangeable handle can also be provided for connection to either of the right-handed and left-handed introducers. In other embodiments, the handle itself exhibits handedness, and separate handles can be provided for each of the right-handed introducer and the left-handed introducer.

In some embodiments, the device is provided in a fully assembled state, while in other embodiments assembly of the device is required. In some embodiments, the device provided in the kit includes a delivery tube having a curved portion at one of its ends configured for insertion into a patient's nostril, wherein the delivery tube is housed within a substantially cylindrical (e.g., pen- or cigar-shaped) housing, such as the type described above. In some embodiments, one or a plurality of the components of the device is disposable and, optionally, biodegradable.

The medicament provided in a kit can contain a single reagent or a plurality of reagents. Representative medicaments for use in accordance with the present teachings include but are not limited to those described above. The medicaments may be provided in packaged combination in the same or in separate containers, depending on their cross-reactivities and stabilities, and in liquid or in lyophilized form. The amounts and proportions of any reagents provided in the kit may be selected so as to provide optimum results for a particular application.

Medicaments included in the kits may be supplied in all manner of containers such that the activities of the different components are substantially preserved, while the components themselves are not substantially adsorbed or altered by the materials of the container. Suitable containers include but are not limited to ampoules, bottles, test tubes, vials, flasks, syringes, bags and envelopes (e.g., foil-lined), and the like. The containers may be formed of any suitable material including but not limited to glass, organic polymers (e.g., polycarbonate, polystyrene, polyethylene, etc.), ceramic, metal (e.g., aluminum), metal alloys (e.g., steel), cork, and the like. In addition, the containers may contain one or more sterile access ports (e.g., for access via a needle), such as may be provided by a septum. Preferred materials for septa include rubber and polymers including but not limited to, for example, polytetrafluoroethylene of the type sold under the trade name TEFLON by DuPont (Wilmington, Del.). In addition, the containers may contain two or more compartments separated by partitions or membranes that can be removed to allow mixing of the components.

Kits in accordance with the present teachings may also be supplied with other items known in the art and/or which may be desirable from a commercial and user standpoint, such as empty syringes, tubing, gauze, pads, disinfectant solution, cleaning solutions, instructions for performing an SPG nerve block and/or for assembling, using, and/or cleaning the device, and the like, and combinations thereof.

In some embodiments, the instructions may be affixed to one or more components of the device and/or the containers (e.g., vials), or to a larger container in which one or more components of the kit are packaged for shipping. The instructions may also be provided as a separate insert, termed the package insert. Instructional materials provided with kits may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail.

The following examples illustrate features of the devices and methods described herein and are provided solely by way of illustration. They are not intended to limit the scope of the appended claims or their equivalents.

EXAMPLES 1-30

The devices and/or methods described above were applied to the treatment of 30 patients suffering from chronic headaches, such as migraine headaches and tension headaches. The results of this testing are surprising and unexpected. By way of illustration, the methods described above resulted in at least 90% reduction in pain and 100% effective SPG block in 100% of the patients. The onset of pain relief ranged from about 30 seconds to about 60 seconds with a duration of pain relief ranging from about 4 to about 24 hours. Each SPG block was performed using only 0.5 cc or less of an anesthetic mixture containing benzocaine, tetracaine, and ropivacaine in amounts described above. In at least 10 of the patients, the duration of the pain relief achieved in accordance with the present teachings exceeded 24 hours. Overall, extremely effective control of headache pain was observed. Patients were able to return to work and avoid toxic pain medications almost 100% of the time.

The devices and methods described herein are applicable for most patients over the age of 15 in 95% of the population—regardless of the patient's height, weight, sex or race. Moreover, although it is presently believed that the devices and methods described herein will primarily be used in the treatment of human patients, these devices and methods can also be applied in the treatment of all manner of non-human patients. Any non-human patient having a nostril (e.g., other mammals such as primates, dogs, cats, pigs, horses, cows, and the like, as well as non-mammals) can likewise be treated (e.g., by a veterinarian) according to the principles set forth herein.

In summary, devices and methods for providing safer and more effective relief from the pain associated with headaches, facial aches, and the like has been described. The devices and methods are economical and can readily be used on patients by trained medical professionals as well as by the patients themselves without supervision from a medical specialist to provide reliable and replicable delivery of medicament to a target location. In some embodiments, the devices and methods described herein may be self-employed by patients twice hourly or as needed.

In use, the optional handle 20 of the devices 10 described herein can be pushed towards the patient's face until introducer 18 snugly and comfortably engages and fits within the patient's nostril to lift the flat tip of the patient's nose to point superiorly and slightly posteriorly. Thereafter, the injector 12 can be pushed posteriorly towards the patient's nose to slide tubular section 24 and nozzle 28 rearwardly until nozzle 28 is located medially and/or posteriorly and/or inferiorly to the SPG—medially and/or inferiorly in some embodiments, and medially, inferiorly, and posteriorly in other embodiments. Thereafter, a medicament such as an anesthetic can be injected and sprayed through apertures 36 of nozzle 28 upwardly and/or laterally and/or anteriorly towards and about the SPG to ameliorate pain—laterally and/or upwardly in some embodiments, and laterally, upwardly, and anteriorly in other embodiments. When an appropriate anesthetic is sprayed onto the SPG, rapid and prolonged vasoconstriction of the blood vessels in the ipsilateral head or brain can be achieved resulting thereafter in effective pain management.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A device for delivering a medicament to a patient in need thereof, the device comprising:
an injector comprising
a first end configured to remain outside a patient's nasal passage and
a second end configured for entry into the patient's nasal passage; and
an introducer configured for engagement into a nostril of the patient and comprising a passageway configured for receiving the injector;
wherein the injector is moveable—relative to the introducer—between a storage position preceding the engagement and an engaging position pursuant to the engagement, where said engaging position is different from the storage position as the injector is extended outward from the introducer; and
wherein the engaging position is configured such that the second end of the injector is situated medial and/or posterior and/or inferior to a sphenopalatine ganglion of a patient;
wherein the second end of the injector comprises one or a plurality of apertures configured for dispersing a medicament superiorly and/or laterally and/or anteriorly towards the sphenopalatine ganglion; and
wherein the injector comprises a channel that extends from the first end to the one or a plurality of apertures at the second end and that is configured to receive a medicament and to communicate the medicament to the one or a plurality of apertures.

2. The device of claim 1 wherein the engaging position is situated medial and inferior to the sphenopalatine ganglion.

3. The device of claim 1 wherein the engaging position is situated medial, inferior, and posterior to the sphenopalatine ganglion.

4. The device of claim 1 wherein the one or a plurality of apertures configured for dispersing a medicament is configured to disperse the medicament laterally and superiorly towards the sphenopalatine ganglion.

5. The device of claim 1 wherein the one or a plurality of apertures configured for dispersing a medicament is configured to disperse the medicament laterally, superiorly, and anteriorly towards the sphenopalatine ganglion.

6. The device of claim 1 wherein the engaging position is situated medial, inferior, and posterior to the sphenopalatine ganglion, and wherein the medicament is dispersed laterally, superiorly, and anteriorly towards the sphenopalatine ganglion.

7. The device of claim 1 further comprising a port in communication with the first end of the injector, wherein the port is configured to receive a syringe containing a medicament.

8. The device of claim 1 further comprising a container in communication with the first end of the injector, wherein the container is configured for containing a medicament.

9. The device of claim 8 wherein the container is squeezable, such that medicament in the container is advanced into the channel by squeezing.

10. The device of claim 8 wherein the container is pressurized.

11. The device of claim 1 wherein the introducer comprises a first portion and a second portion, and wherein a cross-sectional area of the first portion is larger than a cross-sectional area of the second portion.

12. The device of claim 11 wherein the first portion is contoured such that it is configured to be complementary in shape to an interior of the nostril.

13. The device of claim 12 wherein the second introducer portion comprises a substantially flat underside and a rounded convex portion transitioning from the substantially flat underside to the distal terminus of the second introducer portion.

14. The device of claim 1 further comprising a handle connected to the introducer.

15. The device of claim 14 wherein the handle comprises a track configured to receive the passageway of the introducer.

16. The device of claim 15 wherein the handle is configured for movement towards the patient's face, such that posterior movement of the handle moves the introducer into engagement with the nostril of the patient.

17. The device of claim 1 wherein the injector is configured for engagement with a left-side nostril of the patient.

18. The device of claim 17 wherein the introducer is configured for engagement with a left-side nostril of the patient.

19. The device of claim 1 wherein the injector is configured for engagement with a right-side nostril of the patient.

20. The device of claim 19 wherein the introducer is configured for engagement with a right-side nostril of the patient.

21. The device of claim 1 wherein by the engagement of the introducer with the nostril, a horizontal pathway is provided that is substantially parallel to a floor of the patient's nose to a position medial to the patient's inferior turbinate.

22. The device of claim 1 wherein the introducer is configured to be supported by a bottom of the patient's nasal cavity.

23. A method for using the device of claim 1 to deliver the medicament to the patient comprising:
engaging the introducer with the nostril of the patient;
sliding the injector to the engaging position; and
spraying the medicament towards the sphenopalatine ganglion through the one or a plurality of apertures at the second end on the second end of the injector.

24. A method for ameliorating pain in a patient comprising: delivering a medicament superiorly and/or laterally and/or anteriorly towards the sphenopalatine ganglion using the device of claim 1.

25. The method of claim 24 wherein the medicament is delivered laterally and superiorly towards the sphenopalatine ganglion.

26. The method of claim 24 wherein the medicament is delivered laterally, superiorly, and anteriorly towards the sphenopalatine ganglion.

27. The method of claim 24 wherein the patient suffers from a condition selected from the group consisting of sphenopalatine neuralgia, trigeminal neuralgia, glossopharyngeal neuralgia, migraine, migraine with aural headache, migraine without aura headache, tension headache, cluster headache, chronic cluster headache, paroxysmal hemicranias, superior laryngeal neuralgia, facial pain, atypical facial pain, herpes zoster opthalmicus, vasomotor rhinitis, major depression, fibromyalgia, and combinations thereof.

28. The method of claim 24 wherein the method results in increased permeability of the medicament through the blood-brain barrier.

29. The method of claim 24 wherein the pain comprises a headache, a facial ache or a combination thereof.

30. A device for delivering a medicament to a patient in need thereof comprising:
   an injector comprising
      a first end configured to remain outside a nasal passage of the patient,
      a second end configured for entry into the nasal passage of the patient, and
      a channel extending from the first end to the second end and configured for receiving a medicament,
         wherein the second end of the injector comprises one or a plurality of apertures configured for dispersing a medicament superiorly, laterally, and anteriorly towards a sphenopalatine ganglion;
   an introducer configured for engagement into a nostril of the patient and comprising
      a passageway configured for slidably receiving the injector,
      a first portion contoured such that it is configured to be complementary in shape to an interior of the nostril, and
      a second portion comprising a rounded convex portion and a substantially flat underside,
      wherein a cross-sectional area of the first portion is larger than a cross-sectional area of the second portion; and
   a handle connected to the introducer and comprising a track configured to receive the passageway of the introducer;
   wherein the handle is configured for movement towards the patient's face, such that posterior movement of the handle moves the introducer into engagement with the nostril of the patient;
   wherein the injector is moveable—relative to the introducer—between a storage position preceding the engagement and an engaging position pursuant to the engagement, where said engagement position is different from the storage position as the injector is extended outward from the introducer; and
   wherein the engaging position is configured such that the second end of the injector is situated medial, posterior, and inferior to the sphenopalatine ganglion.

* * * * *